US009981898B1

United States Patent
Bui et al.

(10) Patent No.: US 9,981,898 B1
(45) Date of Patent: May 29, 2018

(54) PROCESS FOR OXIDATION OF FATTY ALKENOLS TO ALKENAL PHEROMONE PRODUCTS

(71) Applicant: Provivi, Inc., Santa Monica, CA (US)

(72) Inventors: Vu Bui, Santa Monica, CA (US); Peter Meinhold, Topanga, CA (US); Pedro Coelho, Santa Monica, CA (US); Keith M. Wampler, Santa Monica, CA (US); Michael Cockrem, Madison, WI (US)

(73) Assignee: PROVIVI, INC., Santa Monica, CA (US)

( * ) Notice: Subject to any disclaimer, the term of this patent is extended or adjusted under 35 U.S.C. 154(b) by 0 days. days.

(21) Appl. No.: 15/456,357

(22) Filed: Mar. 10, 2017

Related U.S. Application Data

(60) Provisional application No. 62/306,955, filed on Mar. 11, 2016.

(51) Int. Cl.
C07C 45/30 (2006.01)
C07C 45/86 (2006.01)
B01J 31/02 (2006.01)

(52) U.S. Cl.
CPC .......... C07C 45/30 (2013.01); B01J 31/0271 (2013.01); C07C 45/86 (2013.01); B01J 2231/763 (2013.01); B01J 2531/002 (2013.01); C07B 2200/09 (2013.01)

(58) Field of Classification Search
CPC .................... C07C 45/30; C07C 45/86
USPC ........................................... 568/488
See application file for complete search history.

(56) References Cited

FOREIGN PATENT DOCUMENTS

| | | |
|---|---|---|
| JP | 2014-101306 A | 5/2014 |
| WO | 2015/176020 A1 | 11/2015 |

OTHER PUBLICATIONS

Anelli et al. Fast and Selective Oxidation of Primary Alcohols to Aldehydes or to Carboxylic Acids and of Secondary Alcohols to Ketones Mediated by Oxoammonium Salts under Two-Phase Conditions. Journal of Organic Chemistry, 1987, vol. 52, 2559-2562.*
Ryland et al. Practical Aerobic Oxidations of Alcohols and Amines with Homogeneous Cu/TEMPO and Related Catalyst Systems. Angew. Chem. Int. Ed. Engl. 2014, vol. 53 (34), 8824-8838.*
Bobbit, James M., Oxoammonium Salts. 6.1 4-Acetylamino-2,2,6,6-tetramethylpiperidine-1-oxoammonium Perchlorate: A Stable and Convenient Reagent for the Oxidation of Alcohols. Silica Gel Catalysis, *J. Org. Chem.* 1998, 63, pp. 9367-9374.
Ciriminna et al., Industrial Oxidations with Organocatalyst TEMPO and Its Derivatives, Org. *Process Res Dev.*, 2010, 14, pp. 245-251.
Mamros et al., Oxidation of primary and secondary alcohols by 4-acetylamino-2,2,6,6-tetramethylpiperidine-1-oxoammonium tetrafluoroborate in aqueous media, *ARKIVOC*, 2011, (v) pp. 23-33.
Ryland et al., Practical Aerobic Oxidations of Alcohols and Amines with Homogeneous Cu/TEMPO and Related Catalyst Systems, *Angew Chem Int Ed Engl.*, Aug. 18, 2014, 53(34): pp. 8824-8838.
Zakrzewski et al., Oxidation of Unsaturated Primary Alcohols and ω-Haloalkanols with 4-Acetylamino-2,2,6,6-tetramethylpiperidine-1-oxoammonium Tetrafluoroborate, *Synthesis*, 2007, 16, pp. 2491-2494.

* cited by examiner

*Primary Examiner* — Sikarl A Witherspoon
(74) *Attorney, Agent, or Firm* — Kilpatrick Townsend & Stockton LLP

(57) ABSTRACT

The present invention relates, in part, to an improved process for oxidation of alcohols containing oxidatively sensitive functional groups, using inexpensive reagents under mild reaction conditions to provide high yields of carbonyl products such as aldehydes or ketones. In certain embodiments, an aldehyde product is obtained by contacting an oxidatively sensitive alcohol, such as an alkenol, with an oxidant and a TEMPO catalyst under conditions sufficient to convert the alkenol to the aldehyde.

17 Claims, 1 Drawing Sheet x = 0 to 17
$R^1$ = H, alkyl, alkenyl
$R^2$ = H, alkyl, alkenyl, alkynyl,
aryl, heteroaryl

PROCESS FOR OXIDATION OF FATTY ALKENOLS TO ALKENAL PHEROMONE PRODUCTS

The present application claims priority to U.S. Provisional Pat. Appl. No. 62/306,955, filed Mar. 11, 2016, which application is incorporated herein by reference in its entirety.

BACKGROUND OF THE INVENTION

The oxidation of alcohols to carbonyl compounds is an important transformation in organic chemistry and, as such, numerous preparative methods have been developed for this purpose. Traditionally, oxidation of alcohols is carried out with heavy metal reagents such as chromium (VI), ruthenium, manganese (VII) or with peroxyacids, activated dimethyl sulfoxide (DMSO), and hypervalent iodine. Often, these processes are conducted under harsh reaction conditions with expensive reagents and generate large amounts of toxic waste, rendering them impractical for most large-scale industrial application. Additionally, the reaction conditions generally used in these methods are insensitive to independently reactive functional groups such as unsaturated carbon-carbon bonds, thereby severely limiting their use in synthetic organic chemistry.

Stable tetraalkylnitroxyl radicals, such as 2,2,6,6-tetramethylpiperidine-1-oxyl (TEMPO) have been used for oxidation of organic alcohols as described, for example, by Annelli (*J. Org. Chem.* 1987, 52, 2560) and Ciriminna (*Org. Process Res. Dev.*, 2010, 14, 245). However, known processes employing TEMPO-mediated oxidation for the preparation of carbonyl compounds with labile functional groups, such as alkenes, are generally associated with disadvantages including expensive terminal oxidants (e.g., iodosobenzene diacetate), stoichiometric amounts of TEMPO, environmentally unfriendly chlorinated solvents, and impractically long reaction times. Accordingly, there is a need in the art for alcohol oxidation methods that are high yielding, selective, and robust, yet are conducted under mild reaction conditions and are tolerant of independently reactive functional groups, such as unsaturated carbon-carbon bonds. The present invention satisfies this need and provides other advantages as well.

BRIEF SUMMARY OF THE INVENTION

In one embodiment, the invention provides a method for preparing a compound according to Formula I:

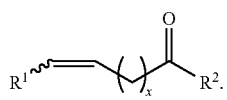
(I)

The method includes:
forming a reaction mixture comprising sodium hypochlorite (NaOCl), a TEMPO catalyst, and an alcohol according to Formula II

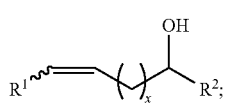
(II)

and
maintaining the reaction mixture under conditions sufficient to form the compound according to Formula I;
wherein:
$R^1$ is selected from the group consisting of H, $C_{1-18}$ alkyl, $C_{2-18}$ alkenyl, $C_{2-18}$ alkynyl;
$R^2$ is selected from the group consisting of H, $C_{1-18}$ alkyl, $C_{2-18}$ alkenyl, $C_{2-18}$ alkynyl, $C_{6-10}$ aryl, and 5- to 10-membered heteroaryl; and
x is an integer from 0 to 17.

In certain embodiments, the TEMPO catalyst is 4-hydroxy-(2,2,6,6-tetramethyl-piperidin-1-yl)oxyl.

Other objects, features, and advantages of the present invention will be apparent to one of skill in the art from the following detailed description and figures.

DETAILED DESCRIPTION OF THE INVENTION

I. Introduction

Figure 1:
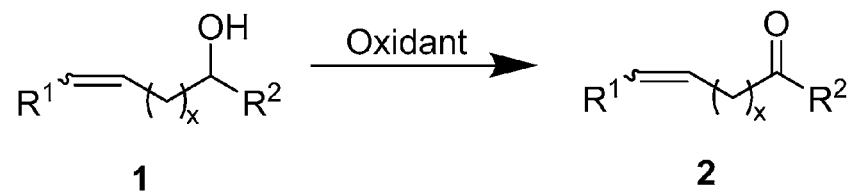
FIG. 1 illustrates the overall reaction scheme of converting an unsaturated alcohol to a carbonyl compound.
Figure 2:
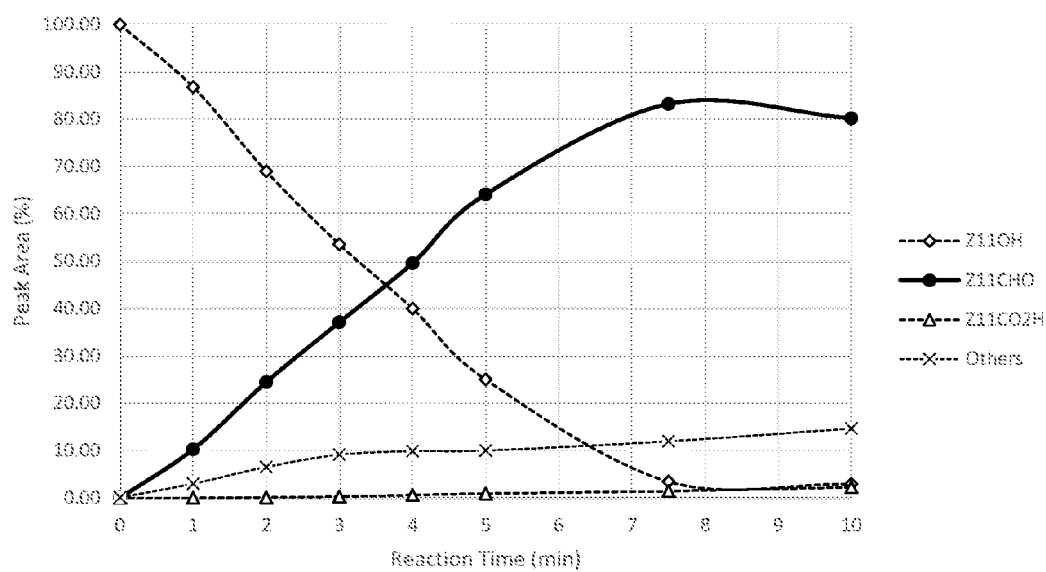
FIG. 2 illustrates a time course experiment of the oxidation of Z11-hexadecenol using TEMPO, showing the distribution of reactants and oxidation products over time. The maximum conversion for the reaction was seen to be about 97% at 7.5 min with a selectivity of 86% for Z11-hexadecenal, 1.5% for Z11-hexadecenoic acid, and 12.4% unknown byproducts. At 10 min the selectivity for Z11-hexadecenal, Z11-hexadecenoic acid, and unknown byproducts were found to be 82%, 2.32%, and 15.1% respectively.

The present invention is based, in part, on the discovery that certain piperidine 1-oxyl catalysts can provide large increases in oxidation yields for the preparation of unsaturated fatty aldehydes and other unsaturated carbonyl compounds. This catalyst activity allows for the use of convenient and non-toxic oxidants, such as bleach, instead of oxidizing agents containing heavy metals or hypervalent iodine. Other advantages of the invention include short reaction times and minimal formation of unwanted byproducts.

II. Definitions

As used herein, the term "TEMPO" refers to 2,2,6,6-tetramethylpiperidine 1-oxyl (CAS No. 2564-83-2). The term "TEMPO catalyst" refers to 2,2,6,6-tetramethylpiperidine 1-oxyl comprising one or more further substituents bonded to the TEMPO piperidine moiety. The term "HO-TEMPO" refers to 4-hydroxy-2,2,6,6-tetramethylpiperidine 1-oxyl (CAS No. 2226-96-2).

As used herein, the term "alkyl" is given its ordinary meaning in the art and includes straight-chain alkyl groups and branched-chain alkyl groups. In certain embodiments, a straight chain or branched chain alkyl has about 1-30 carbon atoms in its backbone (e.g., $C_1$-$C_{30}$ for straight chain, $C_3$-$C_{30}$ for branched chain), and alternatively, about 1-20 carbon atoms or 1-18 carbon atoms. In some embodiments, an alkyl group may be a lower alkyl group, wherein a lower alkyl group comprises 1-4 carbon atoms (e.g., $C_1$-$C_4$ for straight chain lower alkyls).

As used herein, the term "alkenyl" refers to an alkyl group, as defined herein, having one or more carbon-carbon double bonds. The term "heteroalkenyl" refers to an alkenyl group wherein one or more carbon atoms is replaced with a heteroatom (i.e., nitrogen, oxygen, or sulfur, including any oxidized form of nitrogen or sulfur, and any quaternized form of a basic nitrogen). Alkenyl groups include "dienyl" groups having two carbon-carbon double bonds and "trienyl" groups having three carbon-carbon double bonds. Alkenyl groups also include "enynyl" groups having an alkynyl moiety in addition to an alkenyl moiety (i.e., having at least one carbon-carbon double bond and at least one carbon-carbon triple bond).

As used herein, the term "alkynyl" refers to an alkyl group, as defined herein, having one or more triple bonds.

The term "aryl," used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but is not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like. The term "aryloxy" refers to a moiety —OR, wherein R is an aryl group as defined above.

The terms "heteroaryl" and "heteroar-," used alone or as part of a larger moiety, e.g., "heteroaralkyl," or "heteroaralkoxy," refer to groups having 5 to 10 ring atoms (i.e., monocyclic or bicyclic), in some embodiments 5, 6, 9, or 10 ring atoms. In some embodiments, such rings have 6, 10, or 14 pi electrons shared in a cyclic arrangement; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-," as used herein, also include groups in which a heteroaromatic ring is fused to one or more aryl, cycloaliphatic, or heterocyclyl rings, where the radical or point of attachment is on the heteroaromatic ring. Non-limiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3(4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

Examples of aryl and heteroaryl groups include, but are not limited to, phenyl, pyrrolyl, furanyl, thiophenyl, imidazolyl, oxazolyl, thiazolyl, triazolyl, pyrazolyl, pyridinyl, pyrazinyl, pyridazinyl and pyrimidinyl, and the like. It should be understood that, when aryl and heteroaryl groups are used as ligands coordinating a metal center, the aryl and heteroaryl groups may have sufficient ionic character to coordinate the metal center. For example, when a heteroaryl group such as pyrrole is used as a nitrogen-containing ligand, as described herein, it should be understood that the pyrrole group has sufficient ionic character (e.g., is sufficiently deprotonated to define a pyrrolyl) to coordinate the metal center. In some cases, the aryl or heteroaryl group may comprise at least one functional group that has sufficient ionic character to coordinate the metal center, such as a biphenolate group, for example.

As used herein, the terms "forming a reaction mixture" and "contacting" refer to the process of bringing into contact at least two distinct species such that they can react. It should be appreciated, however, that the resulting reaction product can be produced directly from a reaction between the added reagents or from an intermediate from one or more of the added reagents that can be produced in the reaction mixture.

As used herein, the term "phase transfer catalyst" refers to a substance which is at least partially present in a first phase (e.g., an organic phase), or wetted by the first phase, and capable of promoting reaction between a first reactant in the first phase and a second reactant in a second phase (e.g., an aqueous phase). In certain instances, the phase transfer catalyst promotes the reaction by bringing the second reactant from the second phase into the first phase, or by bringing the first reactant from the first phase into the second phase.

The terms "about" and "around," as used herein to modify a numerical value, indicate a close range surrounding that explicit value. If "X" were the value, "about X" or "around X" would indicate a value from 0.9X to 1.1X, and in certain instances, a value from 0.95X to 1.05X or from 0.98X to 1.02X. Any reference to "about X" or "around X" specifically indicates at least the values X, 0.95X, 0.96X, 0.97X, 0.98X, 0.99X, 1.01X, 1.02X, 1.03X, 1.04X, and 1.05X. Thus, "about X" and "around X" are intended to teach and provide written description support for a claim limitation of, e.g., "0.99x."

III. Detailed Description of the Embodiments

In one embodiment, the invention provides a method for oxidizing oxidatively sensitive alcohols to carbonyl compounds. The method includes contacting an oxidatively sensitive alcohol with an oxidant and a TEMPO catalyst for a time sufficient to convert the oxidatively sensitive alcohol to a carbonyl compound. In some embodiments, the oxidatively sensitive alcohol comprises an oxidatively sensitive functional group selected from the group consisting of at least one carbon-carbon double bond, at least one carbon-carbon triple bond, and combinations thereof. In some embodiments, the oxidatively sensitive alcohol comprises at least one carbon-carbon double bond.

In some embodiments, the oxidatively sensitive alcohol is represented by Formula II:

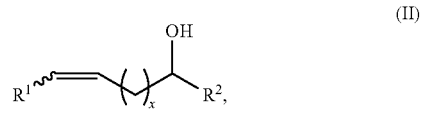

(II)

wherein
R$^1$ is selected from the group consisting of H, C$_{1-18}$ alkyl, C$_{2-18}$ alkenyl, and C$_{2-18}$ alkynyl;

$R^2$ is selected from the group consisting of H, $C_{1-18}$ alkyl, $C_{2-18}$ alkenyl, $C_{2-18}$ alkynyl, $C_{6-10}$ aryl, and 5- to 10-membered heteroaryl; and x is an integer from 0 to 17.

Oxidatively sensitive alcohols comprising at least one carbon-carbon double bond can be prepared as described, for example, in WO 2015/176020, which application is incorporated herein by reference in its entirety for all purposes.

In some embodiments, the alcohol is a decenol or a decadienol. In some embodiments, $R^2$ is H, x is 0, and $R^1$ is $C_7$ alkyl or $C_7$ alkenyl. In some embodiments, $R^2$ is H, x is 2, and $R^1$ is $C_5$ alkyl or $C_5$ alkenyl. In some embodiments, $R^2$ is H, x is 3, and $R^1$ is $C_4$ alkyl or $C_4$ alkenyl.

In some embodiments, the alcohol is an undecenol or an undecadienol. In some embodiments, $R^2$ is H, x is 0, and $R^1$ is $C_8$ alkyl or $C_8$ alkenyl. In some embodiments, the alcohol is a dodecenol or a dodecadienol. In some embodiments, $R^2$ is H, x is 0, and $R^1$ is $C_9$ alkyl or $C_9$ alkenyl. In some embodiments, $R^2$ is H, x is 3, and $R^1$ is $C_6$ alkyl or $C_6$ alkenyl. In some embodiments, $R^2$ is H, x is 4, and $R^1$ is $C_5$ alkyl or $C_5$ alkenyl. In some embodiments, $R^2$ is H, x is 5, and $R^1$ is $C_4$ alkyl or $C_4$ alkenyl. In some embodiments, $R^2$ is H, x is 6, and $R^1$ is $C_3$ alkyl or $C_3$ alkenyl. In some embodiments, $R^2$ is H, x is 7, and $R^1$ is ethyl or ethenyl. In some embodiments, $R^2$ is H, x is 8, and $R^1$ is methyl.

In some embodiments, the alcohol is a tridecenol or a tridecadienol. In some embodiments, $R^2$ is H, x is 2, and $R^1$ is $C_8$ alkyl or $C_8$ alkenyl.

In some embodiments, the alcohol is a tetradecenol or a tetradecadienol. In some embodiments, $R^2$ is H, x is 0, and $R^1$ is $C_{11}$ alkyl or $C_{11}$ alkenyl. In some embodiments, $R^2$ is H, x is 2, and $R^1$ is $C_9$ alkyl or $C_9$ alkenyl. In some embodiments, $R^2$ is H, x is 3, and $R^1$ is $C_8$ alkyl or $C_8$ alkenyl. In some embodiments, $R^2$ is H, x is 5, and $R^1$ is $C_6$ alkyl or $C_6$ alkenyl. In some embodiments, $R^2$ is H, x is 6, and $R^1$ is $C_5$ alkyl or $C_5$ alkenyl. In some embodiments, $R^2$ is H, x is 7, and $R^1$ is $C_4$ alkyl or $C_4$ alkenyl. In some embodiments, $R^2$ is H, x is 8, and $R^1$ is $C_3$ alkyl or $C_3$ alkenyl. In some embodiments, $R^2$ is H, x is 9, and $R^1$ is ethyl or ethenyl.

In some embodiments, the alcohol is a pentadecenol or a pentadecadienol. In some embodiments, $R^2$ is H, x is 4, and $R^1$ is $C_8$ alkyl or $C_8$ alkenyl. In some embodiments, $R^2$ is H, x is 7, and $R^1$ is $C_5$ alkyl or $C_5$ alkenyl. In some embodiments, $R^2$ is H, x is 8, and $R^1$ is $C_4$ alkyl or $C_4$ alkenyl.

In some embodiments, the alcohol is a hexadecenol, a hexadecadienol, or a hexadecatrienol. In some embodiments, $R^2$ is H, x is 2, and $R^1$ is $C_{11}$ alkyl or $C_{11}$ alkenyl. In some embodiments, $R^2$ is H, x is 4, and $R^1$ is $C_9$ alkyl or $C_9$ alkenyl. In some embodiments, $R^2$ is H, x is 5, and $R^1$ is $C_8$ alkyl or $C_8$ alkenyl. In some embodiments, $R^2$ is H, x is 6, and $R^1$ is $C_7$ alkyl or $C_7$ alkenyl. In some embodiments, $R^2$ is H, x is 7, and $R^1$ is $C_6$ alkyl or $C_6$ alkenyl. In some embodiments, $R^2$ is H, x is 8, and $R^1$ is $C_5$ alkyl or $C_5$ alkenyl. In some embodiments, $R^2$ is H, x is 9, and $R^1$ is $C_4$ alkyl or $C_4$ alkenyl. In some embodiments, $R^2$ is H, x is 10, and $R^1$ is $C_3$ alkyl or $C_3$ alkenyl. In some embodiments, $R^2$ is H, x is 12, and $R^1$ is methyl.

In some embodiments, the alcohol is a heptadecenol or a heptadecadienol. In some embodiments, $R^2$ is H, x is 0, and $R^1$ is $C_{14}$ alkyl or $C_{14}$ alkenyl. In some embodiments, $R^2$ is H, x is 7, and $R^1$ is $C_7$ alkyl or $C_7$ alkenyl.

In some embodiments, the alcohol is an octadecenol, an octadecadienol, or an octadecatrienol. In some embodiments, $R^2$ is H, x is 0, and $R^1$ is $C_{15}$ alkyl or $C_{15}$ alkenyl. In some embodiments, $R^2$ is H, x is 1, and $R^1$ is $C_{14}$ alkyl or $C_{14}$ alkenyl. In some embodiments, $R^2$ is H, x is 7, and $R^1$ is $C_8$ alkyl or $C_8$ alkenyl. In some embodiments, $R^2$ is H, x is 9, and $R^1$ is $C_6$ alkyl or $C_6$ alkenyl. In some embodiments, $R^2$ is H, x is 11, and $R^1$ is $C_4$ alkyl or $C_4$ alkenyl. In some embodiments, $R^2$ is H, x is 12, and $R^1$ is $C_3$ alkyl or $C_3$ alkenyl.

In some embodiments, the alcohol according to Formula II is selected from (E)-2-decenol; (Z)-2-decenol; (Z)-4-decenol; (Z)-5-decenol; (E,E)-2,4-decadienol; (E,Z)-2,4-decadienol; (Z,Z)-2,4-decadienol; (E)-2-undecenol; (E)-2-dodecenol; (Z)-5-dodecenol; (E)-6-dodecenol; (E)-7-dodecenol; (Z)-7-dodecenol; (E)-8-dodecenol; (E)-9-dodecenol; (Z)-9-dodecenol; (E)-10-dodecenol; (E,Z)-5,7-dodecadienol; (Z,E)-5,7-dodecadienol; (Z,Z)-5,7-dodecadienol; (E,Z)-7,9-dodecadienol; (E,E)-8,10-dodecadienol; (E,Z)-8,10-dodecadienol; (Z,E)-8,10-dodecadienol; (Z)-4-tridecenol; (E)-5-tetradecenol; (Z)-5-tetradecenol; (Z)-7-tetradecenol; (Z)-8-tetradecenol; (E)-11-tetradecenol; (Z)-11-tetradecenol; (E,E)-2,4-tetradecadienol; (E,Z)-4,9-tetradecadienol; (E,E)-5,8-tetradecadienol; (Z,Z)-5,8-tetradecadienol; (E,E)-8,10-tetradecadienol; (E,Z)-8,10-tetradecadienol; (Z,Z)-8,10-tetradecadienol; (Z,E)-9,11-tetradecadienol; (Z,Z)-9,11-tetradecadienol; (Z,E)-9,12-tetradecadienol; (E,E)-10,12-tetradecadienol; (Z)-10-pentadecenol; (Z,Z)-6,9-pentadecadienol; (E,Z)-9,11-pentadecadienol; (Z,Z)-9,11-pentadecadienol; (Z)-9-hexadecenol; (E)-10-hexadecenol; (Z)-10-hexadecenol; (E)-11-hexadecenol; (Z)-11-hexadecenol; (Z)-12-hexadecenol; (E)-14-hexadecenol; (E)-7-hexadecenol; (Z)-7-hexadecenol; (E)-9-hexadecenol; (E,Z)-4,6-hexadecadienol; (E,Z)-6,11-hexadecadienol; (Z,E)-7,11-hexadecadienol; (Z,Z)-7,11-hexadecadienol; (E,Z)-8,11-hexadecadienol; (E,E)-9,11-hexadecadienol; (E,Z)-9,11-hexadecadienol; (Z,E)-9,11-hexadecadienol; (Z,Z)-9,11-hexadecadienol; (E,E)-10,12-hexadecadienol; (E,Z)-10,12-hexadecadienol; (Z,E)-10,12-hexadecadienol; (Z,Z)-10,12-hexadecadienol; (E,E)-11,13-hexadecadienol; (E,Z)-11,13-hexadecadienol; (Z,E)-11,13-hexadecadienol; (Z,Z)-11,13-hexadecadienol; (E,E)-10,14-hexadecadienol; (E,E,Z)-4,6,11-hexadecatrienol; (E,E,E)-10,12,14-hexadecatrienol; (E,E,Z)-10,12,14-hexadecatrienol; (E,E,Z,Z)-4,6,11,13-hexadecatetraenol; (E)-2-heptadecenol; (Z)-2-heptadecenol; (Z)-9-heptadecenol; (E)-2-octadecenol; (E)-9-octadecenol; (Z)-9-octadecenol; (E)-11-octadecenol; (Z)-11-octadecenol; (E)-13-octadecenol; (Z)-13-octadecenol; (E)-14-octadecenol; (E,Z)-2,13-octadecadienol; (E,Z)-3,13-octadecadienol; (Z,Z)-3,13-octadecadienol; (Z,Z)-9,12-octadecadienol; (Z,Z)-11,13-octadecadienol; (E,E)-11,14-octadecadienol; (Z,Z)-13,15-octadecadienol; and (Z,Z,Z)-9,12,15-octadecatrienol.

Accordingly, some embodiments of the invention provide a method for preparing a compound according to Formula I

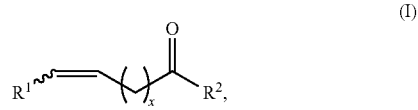

the method comprising:

forming a reaction mixture comprising an sodium hypochlorite (NaOCl), a TEMPO catalyst, and an alcohol according to Formula II

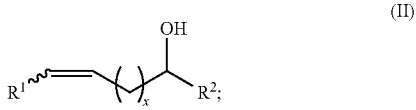

(II)

and
maintaining the reaction mixture under conditions sufficient to form the compound according to Formula I;
wherein:
$R^1$ is selected from the group consisting of H, $C_{1-18}$ alkyl, $C_{2-18}$ alkenyl, $C_{2-18}$ alkynyl;
$R^2$ is selected from the group consisting of H, $C_{1-18}$ alkyl, $C_{2-18}$ alkenyl, $C_{2-18}$ alkynyl, $C_{6-10}$ aryl, and 5- to 10-membered heteroaryl; and
x is an integer from 0 to 17.

Any suitable amount of NaOCl can be used in the methods of the invention. In general, the reaction mixture comprises 1 to 2.5 molar equivalents of NaOCl with respect to the alcohol according to Formula II. For example, the reaction mixture can contain from about 1 equivalent of NaOCl to about 1.25 equivalents of NaOCl, or from about 1.25 equivalents of NaOCl to about 1.5 equivalents of NaOCl, or from about 1.5 equivalents of NaOCl to about 1.75 equivalents of NaOCl, or from about 1.75 equivalents of NaOCl to about 2 equivalents of NaOCl, or from about 2 equivalents of NaOCl to about 2.25 equivalents of NaOCl, or from about 2.25 equivalents of NaOCl to about 2.5 equivalents of NaOCl. The reaction mixture can contain from about 1.2 equivalents of NaOCl to about 1.3 equivalents of NaOCl, or from about 1.15 equivalents of NaOCl to about 1.35 equivalents of NaOCl, or from about 1.1 equivalents of NaOCl to about 1.4 equivalents of NaOCl, or from about 1.05 equivalents of NaOCl to about 1.45 equivalents of NaOCl, or from about 1 equivalent of NaOCl to about 1.5 equivalents of NaOCl.

In some embodiments, the reaction mixture contains from about 1.0 equivalent to about 1.5 equivalents of NaOCl with respect to the alcohol according to Formula II. In some embodiments, the reaction mixture contains from about 1.25 equivalent to about 1.5 equivalents of NaOCl with respect to the alcohol according to Formula II. In some embodiments, the reaction mixture contains from about 1.2 equivalent to about 1.3 equivalents of NaOCl with respect to the alcohol according to Formula II.

Other oxidants can be used in place of or in addition to NaOCl, depending in part on factors such as the structure of the particular alcohol according to Formula II or the particular TEMPO catalyst employed. Examples of suitable oxidants include, but are not limited to, $NaNO_2$, $O_2$, and combinations thereof. Co-catalysts including CuCl, KBr, and the like can be employed with the oxidant and the TEMPO catalyst. In some embodiments, the reaction mixture is free of copper, copper salts (e.g., CuOTf, $CuBr_2$, and the like), and/or copper complexes (e.g., phenanthroline/Cu compex, bipyridine/Cu complex, and the like).

Any suitable amount of oxidant can be used in the methods of the invention. In general, the reaction mixture comprises 1 to 2.5 molar equivalents of the oxidant with respect to the alcohol according to Formula II. For example, the reaction mixture can contain from about 1 equivalent of the oxidant to about 1.25 equivalents of the oxidant, or from about 1.25 equivalents of the oxidant to about 1.5 equivalents of the oxidant, or from about 1.5 equivalents of the oxidant to about 1.75 equivalents of the oxidant, or from about 1.75 equivalents of the oxidant to about 2 equivalents of the oxidant, or from about 2 equivalents of the oxidant to about 2.25 equivalents of the oxidant, or from about 2.25 equivalents of the oxidant to about 2.5 equivalents of the oxidant. The reaction mixture can contain from about 1.2 equivalents of the oxidant to about 1.3 equivalents of the oxidant, or from about 1.15 equivalents of the oxidant to about 1.35 equivalents of the oxidant, or from about 1.1 equivalents of the oxidant to about 1.4 equivalents of the oxidant, or from about 1.05 equivalents of the oxidant to about 1.45 equivalents of the oxidant, or from about 1 equivalent of the oxidant to about 1.5 equivalents of the oxidant.

In some embodiments, the TEMPO catalyst is selected from the group consisting of 4-hydroxy-(2,2,6,6-tetramethylpiperidin-1-yl)oxyl, 4-acetamindo-(2,2,6,6-tetramethylpiperidin-1-yl)oxyl, 4-amino-(2,2,6,6-tetramethylpiperidin-1-yl)oxyl, 4-cyano-(2,2,6,6-tetramethylpiperidin-1-yl)oxyl, 4-carboxy-(2,2,6,6-tetramethylpiperidin-1-yl)oxyl, 4-(2-bromoacetamido)-(2,2,6,6-tetramethylpiperidin-1-yl)oxyl, 4-(2-idodoacetamido)-(2,2,6,6-tetramethylpiperidin-1-yl) oxyl, 4-methoxy-(2,2,6,6-tetramethylpiperidin-1-yl)oxyl, 4-oxo-(2,2,6,6-tetramethylpiperidin-1-yl)oxyl, 4-maleimido-(2,2,6,6-tetramethylpiperidin-1-yl)oxyl; (2,2,6,6-tetramethylpiperidin-1-yl)oxyl methacrylate; and combinations thereof.

In some embodiments the TEMPO catalyst is 4-hydroxy-(2,2,6,6-tetramethylpiperidin-1-yl)oxyl (i.e., HO-TEMPO).

Any suitable amount of the TEMPO catalyst can be used in the methods of the invention. In general, the reaction mixture comprises 0.001 to 1 molar equivalent of the TEMPO catalyst with respect to the alcohol according to Formula II. For example, the reaction mixture can contain from about 0.01 equivalents of the TEMPO catalyst to about 0.05 equivalents of the TEMPO catalyst, or from about 0.05 equivalents of the TEMPO catalyst to about 0.1 equivalents of the TEMPO catalyst, or from about 0.1 equivalents of the TEMPO catalyst to about 0.15 equivalents of the TEMPO catalyst, or from about 0.15 equivalents of the TEMPO catalyst to about 0.2 equivalents of the TEMPO catalyst. The reaction mixture can contain from about 0.01 equivalents of the TEMPO catalyst to about 0.2 equivalents of the TEMPO catalyst, or from about 0.02 equivalents of the TEMPO catalyst to about 0.19 equivalents of the TEMPO catalyst, or from about 0.03 equivalents of the TEMPO catalyst to about 0.18 equivalents of the TEMPO catalyst, or from about 0.04 equivalents of the TEMPO catalyst to about 0.17 equivalents of the TEMPO catalyst, or from about 0.05 equivalents of the TEMPO catalyst to about 0.16 equivalents of the TEMPO catalyst, or from about 0.06 equivalents of the TEMPO catalyst to about 0.15 equivalents of the TEMPO catalyst, or from about 0.07 equivalents of the TEMPO catalyst to about 0.14 equivalents of the TEMPO catalyst, or from about 0.08 equivalents of the TEMPO catalyst to about 0.13 equivalents of the TEMPO catalyst, or from about 0.09 equivalents of the TEMPO catalyst to about 0.12 equivalents of the TEMPO catalyst, or from about 0.09 equivalents of the TEMPO catalyst to about 0.11 equivalents of the TEMPO catalyst, or from about 0.1 equivalents of the TEMPO catalyst to about 0.11 equivalents of the TEMPO catalyst.

In some embodiments, the reaction mixture contains from about 0.01 equivalents to about 0.05 equivalents of TEMPO (i.e., 4-hydroxy-(2,2,6,6-tetramethylpiperidin-1-yl)oxyl). In some embodiments, the reaction mixture contains from about 0.03 equivalents to about 0.05 equivalents of TEMPO. For example, the reaction mixture can contain about 0.01, 0.02, 0.03, 0.04, or 0.05 molar equivalents of TEMPO with respect to the alcohol according to Formula II.

In some embodiments, the reaction mixture contains from about 0.05 equivalents to about 0.15 equivalents of HO-TEMPO. In some embodiments, the reaction mixture contains from about 0.08 equivalents to about 0.12 equivalents of HO-TEMPO. For example, the reaction mixture can contain about 0.05, 0.06, 0.07, 0.08, 0.09, 0.1, 0.11, 0.12, 0.13, 0.14, or 0.15 molar equivalents of HO-TEMPO with respect to the alcohol according to Formula II.

The reaction can be conducted at any suitable temperature for forming the compound of Formula I. In general, the reaction mixture is maintained at a temperature ranging from about −5° C. to about 70° C. The reaction mixture can be maintained, for example, at a temperature ranging from about 15° C. to about 30° C., or from about 18° C. to about 25° C., or from about 20° C. to about 24° C.

The reaction mixture can be maintained under the reaction conditions for any period of time sufficient to form the compound according to Formula I. In general, the reaction mixture is maintained under the reaction conditions for a period of time ranging from about 1 minute to about 60 minutes. For example, the period of time can range from about 1 minute to about 5 minutes, or from about 5 minutes to about 10 minutes, or from about 10 minutes to about 15 minutes, or from about 15 minutes to about 20 minutes, or from about 20 minutes to about 25 minutes, or from about 25 minutes to about 30 minutes, or from about 30 minutes to about 35 minutes, or from about 35 minutes to about 40 minutes, or from about 40 minutes to about 45 minutes, or from about 45 minutes to about 50 minutes, or from about 50 minutes to about 55 minutes, or from about 55 minutes to about 60 minutes. The period of time can range from about 7 minutes to about 9 minutes, or from about 6 minutes to about 10 minutes, or from about 5 minutes to about 11 minutes, or from about 4 minutes to about 12 minutes, or from about 3 minutes to about 13 minutes, or from about 2 minutes to about 14 minutes, or from about 1 minutes to about 15 minutes. For example, the period of time can be about 1, 2, 3, 4, 5, 6, 7, 8, 9, 10, 11, 12, 13, 14, or 15 minutes.

In some embodiments, the reaction mixture is maintained under the conditions sufficient to form the compound according to Formula I for a period of time ranging from about 1 minute to about 30 minutes. In some embodiments, the period of time ranges from about 5 minutes to about 10 minutes. Optionally, termination of the reaction can be achieved by any means known in the art, including quenching, diluting of reaction to reduce the local concentration of reactants and catalysts, centrifugal separation of reaction phases, and/or reducing the temperature of the reaction. Reasons for terminating the reaction before all reactants have reacted include optimizing the yield of the desired product while minimizing the amount of undesired side reactions that can occur.

The reaction mixture can contain further components including, but not limited to, one or more solvents, phase transfer catalysts, and/or buffers. The oxidation reaction in the method described herein is believed to occur via a kinetic process, rather than an equilibrium process, and side reactions can occur in the presence of excess reagents. As described herein, mixing conditions (e.g., interfacial area and phase transfer of reagents between phases) in a biphasic reaction mixture can provide high yields of oxidized products. The mixing conditions can be controlled to stop or slow the oxidation reaction when the oxidized products are obtained in sufficient amounts, allowing for timely isolation of the desired materials.

In some embodiments, the reaction is a bi-phasic solvent system comprising an organic phase and an aqueous phase. The bi-phasic solvent system may be produced by addition of two more immiscible solvents, while in other instances the bi-phasic solvent system may be produced with one or more aqueous solvents and a fatty unsaturated alcohol acting as the organic phase.

In some embodiments, the one or more solvents are selected from the group consisting of $C_5$-$C_{12}$ alkanes, $C_3$-$C_8$ cycloalkanes, alkylesters, aromatic hydrocarbons, ketones, ethers, water, and combinations thereof. In some embodiments, the $C_5$-$C_{12}$ alkanes are selected from the group consisting of pentane, hexane, heptane, octane, and combinations thereof. In some embodiments, the $C_3$-$C_8$ cycloalkanes are selected from the group consisting of cyclopentane, cyclohexane, cycloheptane, and combinations thereof. In some embodiments, the alkylesters are selected from the group consisting of ethyl acetate, isopropyl acetate, and combinations thereof. In some embodiments, the aromatic hydrocarbons are selected from the group consisting of toluene, xylene, cumene, 1,2,4-trimethylbenzene, and combinations thereof. In some embodiments, the ketones are selected from the group consisting of acetone, butanone, pentanone, methyl isopropyl ketone, methyl isobutyl ketone, and combinations thereof. In some embodiments, the ethers are selected from the group consisting of tetrahydrofuran, methyl tert-butyl ether (MTBE), methoxymethane, ethoxyethane, and combinations thereof.

In some embodiments, a poor TEMPO solvent (e.g., toluene, cyclohexane, Aromatic-100 fluid (CAS No. 64742-95-6), or the like), is used in conjunction with a high mixing device to achieve intense phase mixing and a high interfacial area between layers in a biphasic mixture. In some embodiments, a phase transfer catalyst is included. In some embodiments, surfactants may be added or present in the reaction mixture.

In some embodiments, the reaction is performed under high mixing conditions. High mixing conditions can improve the yield and reduce the reaction time of the conversion of an oxidatively sensitive alcohol to a carbonyl compound. In some embodiments, high mixing is advantageous during the reaction phase, but poor mixing is advantageous during a non-reaction phase (e.g., during isolation and/or purification). Devices for achieving useful mixing conditions can include a high shear mixer in tank configuration, a high shear mixer in pump configuration, a high shear mixer in sequential pump and pipe configuration, an inline or static mixing element, a centrifugal contactor, a cuvette flow device, a concentric contactor, a contactor that induces Taylor vortices, and other devices that achieve good liquid-liquid contacting. In some embodiments, the high mixing conditions comprise a rate of stirring above 500 RPM, 600 RPM, 700 RPM, 800 RPM, 900 RPM, or 1000 RPM. The stirring rate ranges from about 1,000 RPM to 10,000 RPM. In some embodiments, the stirring rate ranges from about 3,000 RPM to 4,500 RPM.

In some embodiments, mixing conditions are selected that provide a high shear rate, which promotes droplet formation and increases interfacial surface area. In some embodiments, the use of rotor-stator technology provides high shear mixing. In such cases, mixers are used that utilize a rotor and a stationary stator operating at high rotational speeds that produce high rotor tip speeds with a differential speed between the rotor and the stator that imparts extremely high shear and turbulent energy in the gap between the rotor and stator.

In some embodiments, the high stirring conditions comprise a shear rate of 10,000 to 150,000 s$^{-1}$, e.g., about 45,000-75,000 s$^{-1}$. In some embodiments, the gap distance between the rotor and the stator is less than 200 micrometers, e.g., around 70 micrometers. In some embodiments, the use of a flow reactor technology provides a high degree of mixing and/or a high shear rate. In other embodiments, a flow device is used to provide conditions with a high shear rate of about 10,000 to 150,000 s$^{-1}$, e.g., about 45,000-75,000 s$^{-1}$.

In some embodiments, the pH is maintained in the range of about 8.0-9.0, e.g., in the range of 8.4-8.7. The pH of a reaction mixture is generally maintained using a buffer. In some embodiments, the buffer is selected from the group consisting of NaHCO$_3$, Na$_2$HPO$_4$, KHCO$_3$, K$_2$HPO$_4$, sodium acetate, potassium acetate, and combinations thereof. In some embodiments, the buffer comprises from about 1.0 to 2.0 equivalents of the oxidatively sensitive alcohol.

In some embodiments, slowing or quenching of the reaction is achieved by changing the pH, diluting one or both phases, centrifugal separation of the organic and aqueous phase, cooling one or both of the phases, quenching by adding sodium metabisulfite or sodium thiosulfate, or combinations thereof.

In some embodiments, the rate of forming the preferred carbonyl product is achieved by decreasing the concentration of alcohol and aldehyde in the organic phase and/or decreasing the concentration of oxidant in the aqueous phase. In some embodiments, the concentration of oxidant in the aqueous phase is decreased by using incremental or stepwise addition, such that to some degree the oxidant is added at the same time as it is consumed.

Undesirable side reactions, which are minimized by the methods of the invention, include but are not limited to: the addition of HCl to the unsaturated starting material or product, typically occurring at acidic pH, to form chlorinated side products; over oxidation of aldehyde products to form carboxylic acids; epoxidation of double bonds and subsequent hydrolysis to form hydroxylated species; aldol condensation of aldehydes; addition of alcohols to double bonds to form ethers; condensation of alcohols and aldehydes to form esters; condensation of alcohols and acid byproducts to form esters; and other side reactions.

The methods described herein can increase the rate of unsaturated aldehyde formation relative to the rate of unwanted byproduct formation. In some embodiments, the yield of the aldehyde product is greater than 90% and the rate of aldehyde formation exceeds the rate of byproduct formation by at least 10-fold. In some embodiments, the yield of the aldehyde product is greater than 95% and the rate of aldehyde formation exceeds the rate of byproduct formation by at least 19-fold (e.g., by 20-fold). In some embodiments, the yield of the aldehyde product is greater than 98% and the rate of aldehyde formation exceeds the rate of byproduct formation by at least 49-fold (e.g., by 50-fold).

In some embodiments, the carbonyl compound is converted from the oxidatively sensitive alcohol with a percent yield of at least 80%, e.g., at least about 85%, or at least about 90%. In some the carbonyl compound is converted from the oxidatively sensitive alcohol with a percent yield of at least 81, 82, 83, 84, 85, 86, 87, 88, 89, 90, 91, 92, 93, 94, 95, 96, 97, 98, 99, or 99.9%.

A number of oxidized products can be prepared according to the methods of the invention. In some embodiments, the compound according to Formula I is selected from (E)-2-decenal; (Z)-2-decenal; (Z)-4-decenal; (Z)-5-decenal; (E,E)-2,4-decadienal; (E,Z)-2,4-decadienal; (Z,Z)-2,4-decadienal; (E)-2-undecenal; (E)-2-dodecenal; (Z)-5-dodecenal; (E)-6-dodecenal; (E)-7-dodecenal; (Z)-7-dodecenal; (E)-8-dodecenal; (E)-9-dodecenal; (Z)-9-dodecenal; (E)-10-dodecenal; (E,Z)-5,7-dodecadienal; (Z,E)-5,7-dodecadienal; (Z,Z)-5,7-dodecadienal; (E,Z)-7,9-dodecadienal; (E,E)-8,10-dodecadienal; (E,Z)-8,10-dodecadienal; (Z,E)-8,10-dodecadienal; (Z)-4-tridecenal; (E)-5-tetradecenal; (Z)-5-tetradecenal; (Z)-7-tetradecenal; (Z)-8-tetradecenal; (E)-11-tetradecenal; (Z)-11-tetradecenal; (E,E)-2,4-tetradecadienal; (E,Z)-4,9-tetradecadienal; (E,E)-5,8-tetradecadienal; (Z,Z)-5,8-tetradecadienal; (E,E)-8,10-tetradecadienal; (E,Z)-8,10-tetradecadienal; (Z,Z)-8,10-tetradecadienal; (Z,E)-9,11-tetradecadienal; (Z,Z)-9,11-tetradecadienal; (Z,E)-9,12-tetradecadienal; (E,E)-10,12-tetradecadienal; (Z)-10-pentadecenal; (Z,Z)-6,9-pentadecadienal; (E,Z)-9,11-pentadecadienal; (Z,Z)-9,11-pentadecadienal; (Z)-9-hexadecenal; (E)-10-hexadecenal; (Z)-10-hexadecenal; (E)-11-hexadecenal; (Z)-11-hexadecenal; (Z)-12-hexadecenal; (E)-14-hexadecenal; (E)-7-hexadecenal; (Z)-7-hexadecenal; (E)-9-hexadecenal; (E,Z)-4,6-hexadecadienal; (E,Z)-6,11-hexadecadienal; (Z,E)-7,11-hexadecadienal; (Z,Z)-7,11-hexadecadienal; (E,Z)-8,11-hexadecadienal; (E,E)-9,11-hexadecadienal; (E,Z)-9,11-hexadecadienal; (Z,E)-9,11-hexadecadienal; (Z,Z)-9,11-hexadecadienal; (E,E)-10,12-hexadecadienal; (E,Z)-10,12-hexadecadienal; (Z,E)-10,12-hexadecadienal; (Z,Z)-10,12-hexadecadienal; (E,E)-11,13-hexadecadienal; (E,Z)-11,13-hexadecadienal; (Z,E)-11,13-hexadecadienal; (Z,Z)-11,13-hexadecadienal; (E,E)-10,14-hexadecadienal; (E,E,Z)-4,6,11-hexadecatrienal; (E,E,E)-10,12,14-hexadecatrienal; (E,E,Z)-10,12,14-hexadecatrienal; (E,E,Z,Z)-4,6,11,13-hexadecatetraenal; (E)-2-heptadecenal; (Z)-2-heptadecenal; (Z)-9-heptadecenal; (E)-2-octadecenal; (E)-9-octadecenal; (Z)-9-octadecenal; (E)-11-octadecenal; (Z)-11-octadecenal; (E)-13-octadecenal; (Z)-13-octadecenal; (E)-14-octadecenal; (E,Z)-2,13-octadecadienal; (E,Z)-3,13-octadecadienal; (Z,Z)-3,13-octadecadienal; (Z,Z)-9,12-octadecadienal; (Z,Z)-11,13-octadecadienal; (E,E)-11,14-octadecadienal; (Z,Z)-13,15-octadecadienal; and (Z,Z,Z)-9,12,15-octadecatrienal.

In some embodiments, the carbonyl compound produced is a pheromone or pheromone precursor. In some embodiments, the pheromone is selected from the group consisting of (Z)-7-hexadecenal, (Z)-9-hexadecenal, (Z)-11-hexadecenal, (Z)-13-octadecenal, undecanal, (E)-7-dodecenal, (Z)-9-dodecenal, (E)-11-tetradecenal, (Z)-5-tetradecenal, (Z)-5-tetradecenal(Z)-7-tetradecenal, (Z)-9-tetradecenal, (Z)-10-pentadecenal, (Z)-7-nonadecen-11-one, (E)-6-heneicosen-11-one, (4S,6S,7S)-4,6-dimethyl-7-hydroxynonan-3-one, (Z,Z)-9,11-hexadecadienal, (E,E)-10,12-hexadecadienal, (Z,E)-10,12-hexadecadienal, (E,E)-11,13-hexadecadienal, (E,E,Z)-4,6,11-hexadecatrienal, (Z,Z,E)-7,11,13-hexadecatrienal, (E,E,Z)-10,12,14-hexadecatrienal, (E,Z)-3,13-octadecadienal, (Z,Z)-13,15-octadecadienal, (Z,Z,Z)-9,12,15-octadecatrienal, (Z)-6,14-pentadecadienal, (Z)-9,13-tetradecadien-11-ynal, (Z)-13-hexadecen-11-ynal.

IV. Examples

Z11-hexadecen-1-ol (Bedoukian), NaOCl (Sigma-Aldrich), Na$_2$HPO$_4$ (Sigma-Aldrich), NaHCO$_3$ (Sigma-Aldrich), NaH$_2$PO$_4$ (Sigma-Aldrich), NaOH (Sigma-Aldrich), tetrabutylammonium hydrogensulfate (TBAH, Sigma-Aldrich), TEMPO, HO-TEMPO (Sigma-Aldrich), toluene (Fisher Scientific), and chlorotrimethylsilane/N,O-bis(trimethylsilyl)-trifluoroacetamide (BSTFA+TMCS; Sigma-Aldrich) were used as received from commercial sources. Water was purified using an EMD Millipore Q-Pod system.

Aqueous buffer (pH ~7.8) was prepared by dissolving NaHCO$_3$ (10.08 g), Na$_2$HPO$_4$ (15.3 g), and NaH$_2$PO$_4$ (1.44 g) in 500 mL of H$_2$O. A bleach solution was prepared by combining 10% bleach (47.5 mL) with water (52.5) and adjusting the pH to 10.8. A solution of HOTEMPO was prepared by dissolving HOTEMPO (2070 mg) in toluene (10 mL).

Example 1

Into a 250 mL glass beaker containing 50 mL of buffer solution, tetrabutylammonium hydrogensulfate (TBAH) (407 mg), 30 mL of toluene containing 2.89 g of Z11-hexadecenol (98.2% purity), and 18.3 mg of TEMPO was added. The mixture was stirred via a Silverson Mixer at 4000 RPM and 20 mL of the bleach solution was added via a syringe pump over 90 seconds. With stirring the temperature and pH of the reaction were monitored over the course of 8 minutes. The pH of the reaction is then adjusted to 7.6 with addition of concentrated HCl (~400 The reaction mixture was transferred into a separatory funnel and the Silverson mixing blade was washed with toluene (2×, 50 mL). The combined reaction mixture with the washed toluene was extracted and then allowed to stand undisturbed to achieve phase separation. Aliquot (5 mL) of the organic fraction (127 mL) was dried with anhydrous sodium sulfate and diluted (2×) with fresh toluene containing 2 mg/mL 1-tetradecanol. Aliquot of the sample (0.5 mL) was derivatized with equal volume of BSTFA prior to GC analysis to provide 99% conversion, 65% Z11-16Ald selectivity, and an overall yield of 64%.

Example 2

Into a 250 mL glass beaker containing 50 mL of buffer solution, tetrabutylammonium hydrogensulfate (TBAH) (407 mg), 30 mL of toluene containing 2.89 g of Z11-hexadecenol (98.2% purity), and 1 mL of HO-TEMPO solution (207 mg/mL) was added. The mixture was stirred via a Silverson Mixer at 4000 RPM and 20 mL of the bleach solution was added via a syringe pump over 90 seconds. With stirring the temperature and pH of the reaction were monitored over the course of 8 minutes. The pH of the reaction is then adjusted to 7.5 with addition of concentrated HCl (~400 uL). The reaction mixture was transferred into a separatory funnel and the Silverson mixing blade was washed with toluene (2×, 50 mL). The combined reaction mixture with the washed toluene was extracted and then allowed to stand undisturbed to achieve phase separation. Aliquot (5 mL) of the organic fraction (127 mL) was dried with anhydrous sodium sulfate and diluted (2×) with fresh toluene containing 2 mg/mL 1-tetradecanol. Aliquot of the sample (0.5 mL) was derivatized with equal volume of BSTFA prior to GC analysis to provide 94% conversion, 91% selectivity, and 85% yield of Z11-hexadecenal.

Example 3

Into a 250 mL glass beaker containing 50 mL of buffer solution, tetrabutylammonium hydrogensulfate (TBAH) (407 mg), 30 mL of toluene containing 2.95 g (12.5 mmol) of Z11-hexadecenol, and 203 mg (1.2 mmol) of HOTEMPO in 1 mL of toluene was added. The mixture was stirred via a Silverson Mixer at 4000 RPM and 25 mL (16.8 mmol) of the bleach solution (5%) was added via a syringe pump over 90 seconds and allowed to stir for 10 min at ambient temperature. The reaction mixture was transferred into a separatory funnel and the Silverson mixing blade was washed with toluene (2×, 50 mL). The combined reaction mixture with the washed toluene was extracted and then allowed to stand undisturbed to achieve phase separation. Aliquot (5 mL) of the organic fraction (125 mL) was dried with anhydrous sodium sulfate and diluted (2×) with fresh toluene containing 2 mg/mL 1-tetradecanol. Aliquot of the sample (0.5 mL) was derivatized with equal volume of BSTFA prior to GC analysis to provide 79% conversion, 84% selectivity for Z11-16Ald, and an overall yield of 67%.

Example 4

Into a 250 mL glass beaker containing 50 mL of buffer solution, tetrabutylammonium hydrogensulfate (TBAH) (407 mg), 30 mL of toluene containing 2.95 g of Z11-hexadecenol, and 203 mg of HOTEMPO in 1 mL of toluene was added. The mixture was stirred via a Silverson Mixer at 4000 RPM and 20 mL of the bleach solution (5%) was added via a syringe pump over 90 seconds and allowed to stir for 10 min at ambient temperature. The reaction mixture was transferred into a separatory funnel and the Silverson mixing blade was washed with toluene (2×, 50 mL). The combined reaction mixture with the washed toluene was extracted and then allowed to stand undisturbed to achieve phase separation. Aliquot (5 mL) of the organic fraction (125 mL) was dried with anhydrous sodium sulfate and diluted (2×) with fresh toluene containing 2 mg/mL 1-tetradecanol. Aliquot of the sample (0.5 mL) was derivatized with equal volume of BSTFA prior to GC analysis to provide 71% conversion, 97% Z11-16Ald selectivity, and an overall yield of 69%.

Example 5

Into a 250 mL glass beaker containing 50 mL of buffer solution, tetrabutylammonium hydrogensulfate (TBAH) (407 mg), 30 mL of toluene containing 2.95 g of Z11-hexadecenol, and 203 mg of HOTEMPO in 1 mL of toluene was added. The mixture was stirred via a Silverson Mixer at 4000 RPM and 20 mL of the bleach solution (5%) was added via a syringe pump over 90 seconds and allowed to stir for 17 min at ambient temperature. The reaction mixture was transferred into a separatory funnel and the Silverson mixing blade was washed with toluene (2×, 50 mL). The combined reaction mixture with the washed toluene was extracted and then allowed to stand undisturbed to achieve phase separation. Aliquot (5 mL) of the organic fraction (125 mL) was dried with anhydrous sodium sulfate and diluted (2×) with fresh toluene containing 2 mg/mL 1-tetradecanol. Aliquot of the sample (0.5 mL) was derivatized with equal volume of BSTFA prior to GC analysis to provide 77% conversion, 89% Z11-16Ald selectivity, and an overall yield of 68%.

TABLE 1

Preparation of Z-11-hexadecenal via TEMPO- and HO-TEMPO-catalyzed bleach oxidation.

| Example | TEMPO (eq) | HO-TEMPO (eq) | NaOCl (eq) | Rxn Temp (° C.) | Rxn Time (min) | Conv. (%) | Selectivity (%) | Yield (%) |
|---|---|---|---|---|---|---|---|---|
| 1 | 0.01 | — | 1.25 | 20-22 | 8 | 99 | 65 | 64.4 |
| 2 | — | 0.1 | 1.25 | 20-22 | 8 | 94 | 91 | 85.5 |
| 3 | — | 0.1 | 1.35 | 20-24 | 8 | 79 | 84 | 66.8 |
| 3a | — | 0.1 | 1.51 | 20-24 | 8 | 83 | 87 | 72.1 |

TABLE 1-continued

Preparation of Z-11-hexadecenal via TEMPO- and HO-TEMPO-catalyzed bleach oxidation.

| Example | TEMPO (eq) | HO-TEMPO (eq) | NaOCl (eq) | Rxn Temp (° C.) | Rxn Time (min) | Conv. (%) | Selectivity (%) | Yield (%) |
|---|---|---|---|---|---|---|---|---|
| 4 | — | 0.1 | 1.08 | 20-24 | 8 | 71 | 97 | 68.8 |
| 5 | — | 0.1 | 1.08 | 17-18 | 15 | 77 | 89 | 68.4 |

High yields (82%-85%) of the desired product, Z11-hexadecenal were obtained when 0.1 equivalent of HO-TEMPO and 1.25 equivalent of terminal oxidant, NaOCl, were used at ambient temperature with 8 min of reaction time. See, e.g., Example 2 in Table 1. Surprisingly, the use of TEMPO resulted in 99% conversion of the starting material but a low yield of the desired product. In contrast, the use of HO-TEMPO resulted in lower conversion of the starting material but a higher selectivity that ultimately provided the desired product in higher yield. This unexpected difference provided a 30% improvement in yield, enabling the use of a bleach as a terminal oxidant rather than the toxic oxidizing agents typically used for industrial preparation of unsaturated aldehydes and related products.

V. Exemplary Embodiments

Exemplary embodiments provided in accordance with the presently disclosed subject matter include, but are not limited to, the claims and the following embodiments:

1. A method for preparing a compound according to Formula I

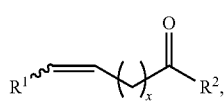

(I)

the method comprising:
forming a reaction mixture comprising sodium hypochlorite (NaOCl), a TEMPO catalyst, and an alcohol according to Formula II

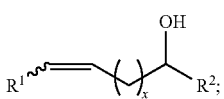

(II)

and
maintaining the reaction mixture under conditions sufficient to form the compound according to Formula I; wherein:
$R^1$ is selected from the group consisting of H, $C_{1-18}$ alkyl, $C_{2-18}$ alkenyl, and $C_{2-18}$ alkynyl;
$R^2$ is selected from the group consisting of H, $C_{1-18}$ alkyl, $C_{2-18}$ alkenyl, $C_{2-18}$ alkynyl,
$C_{6-10}$ aryl, and 5- to 10-membered heteroaryl; and
x is an integer from 0 to 17.
2. The method of embodiment 1, wherein $R^2$ is H.
3. The method of embodiment 1 or embodiment 2, wherein $R^1$ $C_{1-18}$ alkyl or $C_{2-18}$ alkenyl.
4. The method of any one of embodiments 1 to 4, wherein the reaction mixture comprises 1.0 to 1.5 molar equivalents of NaOCl with respect to the alcohol according to Formula II.
5. The method of any one of embodiments 1 to 4, wherein the TEMPO catalyst is selected from the group consisting of 4-hydroxy-(2,2,6,6-tetramethylpiperidin-1-yl)oxyl; 4-acetamindo-(2,2,6,6-tetramethylpiperidin-1-yl)oxyl; 4-amino-(2,2,6,6-tetramethylpiperidin-1-yl)oxyl; 4-cyano-(2,2,6,6-tetramethylpiperidin-1-yl)oxyl; 4-carboxy-(2,2,6,6-tetramethyl-piperidin-1-yl)oxyl; 4-(2-bromoacetamido)-(2,2,6,6-tetramethylpiperidin-1-yl)oxyl; 4-(2-idodoacetamido)-(2,2,6,6-tetramethyl-piperidin-1-yl)oxyl; 4-methoxy-(2,2,6,6-tetramethyl-piperidin-1-yl)oxyl; 4-oxo-(2,2,6,6-tetramethylpiperidin-1-yl)oxyl; 4-maleimido-(2,2,6,6-tetramethylpiperidin-1-yl)oxyl; (2,2,6,6-tetramethylpiperidin-1-yl)oxyl methacrylate; and combinations thereof.
6. The method of embodiment 5, wherein the TEMPO catalyst is 4-hydroxy-(2,2,6,6-tetramethylpiperidin-1-yl)oxyl.
7. The method of any one of embodiments 1 to 6, wherein the reaction mixture comprises no more than 0.1 molar equivalents of the TEMPO catalyst with respect to the alcohol according to Formula II.
8. The method of embodiment 7, wherein the reaction mixture comprises no more than 0.05 molar equivalents of the TEMPO catalyst with respect to the alcohol according to Formula II.
9. The method of any one of embodiments 1 to 8, wherein the reaction mixture is maintained under the conditions sufficient to form the compound according to Formula I for a period of time ranging from about 1 minute to about 30 minutes.
10. The method of embodiment 9, wherein the period of time ranges from about 5 minutes to about 10 minutes.
11. The method of any one of embodiments 1 to 10, further comprising stirring the reaction mixture at a stir rate ranging from about 1,000 RPM to about 10,000 RPM.
12. The method of any one of embodiments 1 to 11, wherein the reaction mixture further comprises one or more components selected from the group consisting of a phase transfer catalyst, a buffer, and a solvent.
13. The method of embodiment 12, wherein the solvent comprises an organic phase and an aqueous phase.
14. The method of embodiment 12 or embodiment 13, wherein the phase transfer catalyst is selected from the group consisting of tetrabutylammonium chloride (n-Bu$_4$NCl), tetrabutylammonium bromide (n-Bu$_4$NBr), tetrabutylammonium sulfate (n-Bu$_4$NHSO$_4$), tricaprylylmethylammonium chloride, and combinations thereof.
15. The method of any one of embodiments 12 to 14, wherein the reaction mixture comprises from about 0.01 to about 0.1 molar equivalents of the phase transfer catalyst with respect to the alcohol according to Formula II.
16. The method of any one of embodiments 12 to 15, wherein the buffer is selected from the group consisting of NaHCO$_3$, Na$_2$HPO$_4$ Na$_2$HPO$_4$, sodium acetate, KHCO$_3$, K$_2$HPO$_4$ K$_2$HPO$_4$, potassium acetate, and combinations thereof.
17. The method of any one of embodiments 12 to 16, wherein the pH of the reaction mixture ranges from about 8.0 to about 9.0.
18. The method of any one of embodiments 1 to 17, wherein the reaction mixture is maintained at a temperature ranging from about 18° C. to about 25° C.

Although the foregoing has been described in some detail by way of illustration and example for purposes of clarity and understanding, one of skill in the art will appreciate that certain changes and modifications can be practiced within the scope of the appended claims. All publications, patents, patent applications, and sequence accession numbers cited herein are hereby incorporated by reference in their entirety for all purposes.

What is claimed is:

1. A method for preparing a compound according to Formula

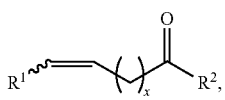

the method comprising:
forming a reaction mixture comprising sodium hypochlorite (NaOCl), a TEMPO catalyst, and an alcohol according to Formula II

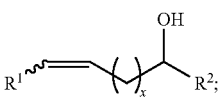

and
maintaining the reaction mixture under conditions sufficient to form the compound according to Formula I;
wherein:
$R^1$ is selected from the group consisting of H, $C_{1-18}$ alkyl, $C_{2-18}$ alkenyl, and $C_{2-18}$ alkynyl;
$R^2$ is H; and
x is an integer from 0 to 17.

2. The method of claim 1, wherein $R^1$ $C_{1-18}$ alkyl or $C_{2-18}$ alkenyl.

3. The method of claim 1, wherein the reaction mixture comprises 1.0 to 1.5 molar equivalents of NaOCl with respect to the alcohol according to Formula II.

4. The method of claim 1, wherein the TEMPO catalyst is selected from the group consisting of 4-hydroxy-(2,2,6,6-tetramethylpiperidin-1-yl)oxyl; 4-acetamindo-(2,2,6,6-tetramethylpiperidin-1-yl)oxyl; 4-amino-(2,2,6,6-tetramethyl-piperidin-1-yl)oxyl; 4-cyano-(2,2,6,6-tetramethylpiperidin-1-yl)oxyl; 4-carboxy-(2,2,6,6-tetramethyl-piperidin-1-yl)oxyl; 4-(2-bromoacetamido)-(2,2,6,6-tetramethylpiperidin-1-yl)oxyl; 4-(2-idodoacetamido)-(2,2,6,6-tetramethylpiperidin-1-yl)oxyl; 4-methoxy-(2,2,6,6-tetramethyl-piperidin-1-yl)oxyl; 4-oxo-(2,2,6,6-tetramethylpiperidin-1-yl)oxyl; 4-maleimido-(2,2,6,6-tetramethylpiperidin-1-yl)oxyl; (2,2,6,6-tetramethylpiperidin-1-yl)oxyl methacrylate; and combinations thereof.

5. The method of claim 4, wherein the TEMPO catalyst is 4-hydroxy-(2,2,6,6-tetramethylpiperidin-1-yl)oxyl.

6. The method of claim 1, wherein the reaction mixture comprises no more than 0.1 molar equivalents of the TEMPO catalyst with respect to the alcohol according to Formula II.

7. The method of claim 6, wherein the reaction mixture comprises no more than 0.05 molar equivalents of the TEMPO catalyst with respect to the alcohol according to Formula II.

8. The method of claim 1, wherein the reaction mixture is maintained under the conditions sufficient to form the compound according to Formula I for a period of time ranging from about 1 minute to about 30 minutes.

9. The method of claim 8, wherein the period of time ranges from about 5 minutes to about 10 minutes.

10. The method of claim 1, further comprising stirring the reaction mixture at a stir rate ranging from about 1,000 RPM to about 10,000 RPM.

11. The method of claim 1, wherein the reaction mixture further comprises one or more components selected from the group consisting of a phase transfer catalyst, a buffer, and a solvent.

12. The method of claim 11, wherein the solvent comprises an organic phase and an aqueous phase.

13. The method of claim 11, wherein the phase transfer catalyst is selected from the group consisting of tetrabutylammonium chloride (n-Bu$_4$NCl), tetrabutylammonium bromide (n-Bu$_4$NBr), tetrabutylammonium sulfate (n-Bu$_4$NHSO$_4$), tricaprylylmethylammonium chloride, and combinations thereof.

14. The method of claim 13, wherein the reaction mixture comprises from about 0.01 to about 0.1 molar equivalents of the phase transfer catalyst with respect to the alcohol according to Formula II.

15. The method of claim 11, wherein the buffer is selected from the group consisting of NaHCO$_3$, Na$_2$HPO$_4$, Na$_2$HPO$_4$, sodium acetate, KHCO$_3$, K$_2$HPO$_4$ K$_2$HPO$_4$, potassium acetate, and combinations thereof.

16. The method of claim 15, wherein the pH of the reaction mixture ranges from about 8.0 to about 9.0.

17. The method of claim 1, wherein the reaction mixture is maintained at a temperature ranging from about 18° C. to about 25° C.

* * * * *